United States Patent [19]

Shaer

[11] Patent Number: 4,548,727

[45] Date of Patent: Oct. 22, 1985

[54] AQUEOUS COMPOSITIONS CONTAINING STABILIZED ENZYMES

[75] Inventor: Elias H. Shaer, Cincinnati, Ohio

[73] Assignee: The Drackett Company, Cincinnati, Ohio

[21] Appl. No.: 539,515

[22] Filed: Oct. 6, 1983

[51] Int. Cl.[4] .................... C11D 3/386; C11D 3/20; C12N 9/96; C12R 1/125

[52] U.S. Cl. .................... 252/171; 252/170; 252/173; 252/174.12; 252/174.21; 252/132; 252/122; 252/DIG. 12; 435/188; 435/839

[58] Field of Search .................... 252/174.12, 174, 172, 252/DIG. 12, DIG. 14, 170; 435/188

[56] References Cited

U.S. PATENT DOCUMENTS

| | | | |
|---|---|---|---|
| 3,023,168 | 2/1962 | Doan | 252/137 |
| 3,296,094 | 1/1967 | Coyle | 195/63 |
| 3,532,599 | 10/1970 | Cooperman | 195/3 |
| 3,557,002 | 1/1971 | McCarty | 252/89 |
| 3,575,864 | 4/1971 | Innerfield | 252/89 |
| 3,600,318 | 8/1971 | Mast | 252/99 |
| 3,676,374 | 7/1972 | Zaki et al. | 252/551 |
| 3,682,842 | 8/1972 | Innerfield | 252/539 |
| 3,746,649 | 7/1973 | Barrett, Jr. | 252/170 |
| 3,813,342 | 5/1974 | Cooperman | 252/170 |
| 3,869,399 | 3/1975 | Collins | 252/118 |
| 3,953,353 | 3/1976 | Barrett, Jr. et al. | 252/174 |
| 4,021,377 | 5/1977 | Borchert et al. | 252/546 |
| 4,111,855 | 9/1978 | Barrat et al. | 252/545 |
| 4,142,999 | 3/1979 | Bloching et al. | 252/544 |
| 4,169,817 | 10/1979 | Weber | 252/545 |
| 4,243,543 | 1/1981 | Guilbert et al. | 252/105 |
| 4,243,546 | 1/1981 | Shaer | 252/174.12 |
| 4,261,868 | 4/1981 | Hora et al. | 252/529 |
| 4,287,082 | 9/1981 | Tolfo et al. | 252/174.12 |
| 4,318,818 | 3/1982 | Letton et al. | 252/174.12 |

*Primary Examiner*—Lionel M. Shapiro
*Assistant Examiner*—Rebecca L. Thompson
*Attorney, Agent, or Firm*—Charles Zeller

[57] ABSTRACT

An aqueous enzyme preparation stabilized with an ester of the formula RCOOR′ where R is an alkyl of from one to three carbons or hydrogen and R′ is an alkyl of from one to six carbons, the ester being in an amount of from 0.1 to about 2.5% by weight.

20 Claims, No Drawings

AQUEOUS COMPOSITIONS CONTAINING STABILIZED ENZYMES

BACKGROUND OF THE INVENTION

This invention relates to long term stabilization of an enzyme contained in an aqueous composition by a lower molecular weight organic ester.

The desirability of using enzymes of the proteolytic and alpha amylolytic type in cleaning compositions is well known. These enzymes are useful for their ability to reduce macromolecules such as proteins and starches into smaller molecules so that they can be readily washed away by detergents and/or water. Specifically, the proteolytic enzymes are useful in breaking down proteins and the alpha amylolytic enzymes are useful in breaking down carbohydrates. Detergent compositions containing these enzymes have a wide variety of uses in that they are capable of removing proteinaceous and starchy stains such as egg stains, blood stains, gravy stains, and the like.

Detergent compositions containing enzymes have been commercially available in dry powdered form. However, there are inherent problems with these compositions. First, they must be stored in such a way as to be protected from humidity and high heat to insure enzyme stability. Second, these dry powdered compositions are not well suited for several useful applications such as spot cleaners, laundry presoaks and prespotters, which require direct application to the stained surface. For these and other applications it is desirable to have a liquid enzyme composition. It is also advantageous to include significant amounts of water in liquid enzyme compositions for economic as well as processing considerations. However, an inherent problem exists in adding significant amounts of water to an enzyme containing composition in that enzymes are inherently unstable in the presence of water resulting in a rapid decrease of enzymatic activity, i.e., the ability of the enzyme to effectively reduce macromolecules into smaller molecules. It is speculated that the loss in enzymatic activity is due to the hydrolyzing action of water on the enzyme.

Further decreases in enzymatic activity will also result from exposing the aqueous enzyme containing compositions to temperatures in excess of 70° C. In fact, if these compositions are exposed to these temperatures for more than a few hours, complete deactivation will occur.

Therefore, in order to have an aqueous based enzyme containing composition which is suitable for the uses described above, it is clear that the enzyme must not only remain stable in water, i.e. retain its enzymatic activity, but it must also be capable of maintaining such stability for extended periods of time at elevated temperatures, i.e., up to about 100° F. It is not uncommon to have commercial products stored in warehouses for a period of time before being sold to consumers, where the temperatures during storage may exceed normal room temperature.

Various attempts have been made to stabilize enzymes contained in aqueous compositions. The following are exemplary of these.

U.S. Pat. No. 3,296,094 to Cayle utilizes a partially hydrolyzed and solubilized collagen, and glycerol to stabilize an aqueous proteolytic enzyme composition. The amount of glycerol required for stabilization in this composition is between 35% to 60% by weight of the total composition.

U.S. Pat. No. 3,557,002 to McCarty utilizes a monohydroxy alcohol or an alkoxy alcohol to stabilize a proteolytic enzyme. Although the amount of alcohol used in this composition is less than that used in Cayle the residual activity of the enzyme of this composition decreases after long periods of storage at relatively high temperatures.

U.S. Pat. No. 4,169,817 to Weber utilizes either water soluble salts such as sodium or potassium sulfates or chlorides and/or glycerol or alkylene glycols to stabilize a proteolytic enzyme in compositions containing ionic builders and surfactants. Again, significant amounts of glycerol and/or other solids are required to maintain long term enzyme stability in these compositions.

U.S. Pat. No. 3,682,842 to Innerfield utilizes a composition comprising an enzyme-ion binding agent such as trichloroacetic acid or tungstic acid and at least two of: a salt, such as sodium chloride or ammonium sulfate; an organic solvent such as ethanol, and an anionic surfactant, to stabilize a mixture of proteolytic and amylolytic enzymes.

U.S. Pat. No. 3,676,374 to Zaki et al utilizes a mixture of alkane sulfonates or alpha olefin sulfonate compounds, along with an alkyl alkyleneoxy hydroxyl or sulfate compounds to stabilize a proteolytic enzyme in a liquid detergent composition containing water. Additionally, various stabilizing agents can be employed with these compositions such as the water-soluble calcium and magnesium chloride lactates and acetates.

Barrett, Jr., in U.S. Pat. No. 3,746,649 discloses a liquid enzyme product stable against proteolytic degradation, the product consisting essentially of an enzyme and 100 to 500 parts per part of the enzyme of an organic medium free of glycerine, the medium being selected from the group of certain of the following: alcohols; alkylene glycols; alkylene glycol alkyl or phenyl ethers; alkylene glycol esters; alkoxy ethanols, propanols and triglycols, and ketones.

In U.S. Pat. No. 3,953,353 to Barrett, Jr., et al, a solid product for rub-on application is disclosed. In U.S. Pat. No. 4,111,855, Barrat et al discloses a liquid enzyme containing detergent composition containing as the stability enhancing system 0.05 to 1.5% by weight of a polyacid capable of forming water-soluble Ca-complexes; from 0.5 to 15 millimol/liter of free calcium ions, and a liquid carrier of water and a lower aliphatic alcohol. The '855 Barrat et al patent teaches that the enzyme stability for a given level of polyacid is inversely related to the logarithm of the stability constant of the Ca-polyacid complexes at the pH of the composition.

Applicant herein, in his earlier issued U.S. Pat. No. 4,243,546 teaches that an alkanolamine in combination with an organic or inorganic acid improves the enzyme stability of aqueous enzyme containing detergent compositions. In Shaer copending patent application U.S. Ser. No. 414,552, filed Sept. 3, 1982, which application is a continuation of U.S. Ser. No. 173,779 filed July 30, 1980, now abandoned, the applicant herein discloses stabilization of enzyme containing detergent compositions with a stabilizer system containing a salt of a low molecular weight carboxylic acid in the presence of an alkyl alcohol of from one to six carbon atoms.

U.S. Pat. No. 4,287,082 to Tolfo discloses that homogeneous aqueous enzyme containing liquid detergent compositions containing substantial levels of saturated fatty acids may be stabilized with minute amounts of enzyme accessible calcium, and additive levels of selected short chain carboxylic acids. Similarly, Letton in U.S. Pat. No. 4,318,818 discloses a stabilizing system comprising calcium ions and a low molecular weight carboxylic acid or salt, preferably a formate, and preferably in the presence of a low molecular weight alcohol, the pH being in the range of from about 6.5 to about 10.

Stabilization of enzyme containing compositions is also discussed in U.S. Pat. Nos. 3,600,318 to Mast; 4,261,868 to Hora et al; 4,142,999 to Bloching et al; 4,243,543 to Guilbert et al; 3,532,599 and 3,813,342 to Cooperman; 3,869,399 to Collins; 3,575,864 to Innerfield, and 3,023,168 to Doan.

In U.S. Pat. No. 3,532,599 to Cooperman, a cleaning composition is disclosed for removing printing ink from rubber rollers, the composition optionally including any inert diluent that does not deactivate the enzyme. The organic solvents that may be included include aromatic solvents, e.g., benzene, aliphatic hydrocarbons such as hexane, or other solvents such as ethanol ethyl acetate or ether. No discussion is provided concerning the effect of these solvents or diluents on stability. Rather, Cooperman states that the enzyme is compatible with these materials.

SUMMARY OF THE INVENTION

It is an object of this invention to provide aqueous based compositions containing stabilized enzymes which are suitable for use as cleaners where the enzymes will be stabilized, i.e. maintain their activity, for long periods of time. It is a further object of this invention to provide such stability by using small amounts of a relatively inexpensive stabilizing agent.

The compositions of this invention require only minor amounts of an enzyme stabilizing agent to achieve superior long term enzyme stability which will be maintained even at elevated temperatures, i.e., temperatures up to about 100° F., as may be encountered under an adverse storage environment. These compositions are particularly effective as cleaning preparations in a wide range of applications.

The compositions of this invention are comprised of the following ingredients (all amounts given below and throughout this application are on a weight basis):

(a) from about 0.1 to about 2.5% of an enzyme stabilizing agent which is an ester of the formula RCOOR′ where R is an alkyl radical of 1 to 3 carbon atoms or hydrogen and R′ is an alkyl radical of 1 to 6 carbon atoms;

(b) from about 0.006% to about 5% of an active enzyme selected from the group consisting of proteases, alpha amylases and mixtures thereof, said enzyme being provided in pure form or as incorporated within a commercial enzyme preparation comprising from about 2 to about 80% of said enzyme and from about 20 to 98% of a carrier therefor, and (c) the remainder water.

DETAILED DESCRIPTION OF THE PREFERRED EMBODIMENT

In accordance with the present invention, it has been found that esters having the general formula RCOOR′ wherein R is an alkyl radical of one to three carbon atoms or hydrogen and R′ is an alkyl radical of one to six carbon atoms can stabilize proteolytic or amylolytic enzymes or mixtures thereof in an aqueous medium. It has also been found that the enzyme thus stabilized will retain its activity for an extended period of time, in the order of one year to eighteen months.

The main ingredients of the compositions of this invention are water, enzymes and the ester stabilizing agent.

Water can comprise from about 10% to about 90% of the total composition of the present invention. Preferably water will be present in amounts ranging from about 40% to about 90% by weight. Although not mandatory deionized water is preferred for use herein.

The enzymes which are stabilized by and therefore suitable for use in the present invention are the proteases, the alpha amylases and mixtures of proteases and alpha amylases.

The proteases which are derived from bacterial or fungal sources can be classified into three different categories: acidic, neutral, and alkaline proteases, all of which are useful herein. Proteases derived from plant and animal sources, although not readily classifiable into the above recited categories, are also useful herein. These enzymes are active in pH's ranging from about 3 to 11, although optimum activity of these enzymes is generally exhibited in the pH range of about 6 to 9. The proteases catalyze the hydrolysis of the peptide linkages of proteins, polypeptides and other related compounds. By breaking the peptide bonds of proteins, free amino and carboxy groups are formed which are short chain molecules that can easily be washed away by water and/or a detergent. All categories of proteases enumerated above are useful in this invention, however, those having optimum activity in pH's ranging from about 6 to about 9 are preferred. An example of a preferred protease is a serine protease.

The alpha amylases exhibit optimum activity in the acidic pH ranges. These enzymes catalyze reactions which break starch molecules into shorter chain molecules that are readily washed away by detergents and/or water. The alpha amylases may be obtained from animal sources, cereal grains, or bacterial and fungal sources.

The enzyme ingredient of the present invention can be conveniently added in the form of a commercial enzyme preparation. These are generally sold in a dry powder, solution, or slurry form and are comprised of from about 2% to about 80% of active enzymes in combination with a carrier such as sodium or calcium sulfate, sodium chloride, glycerol, nonionic surfactants, or mixtures thereof as the remaining 20% to 98%. Examples of commercial protease preparations which are suitable for use in the compositions of this invention include Savinase, e.g., Savinase 8.0 Slurry; Esperase, e.g., Esperase 8.0 Slurry, and Alcalase, all from Novo Industri A/S, Copenhagen, Denmark; and High Alkaline Protease, e.g., Alkaline Protease 201 P and Maxatase P, all from G.B. Fermentation Inc., Des Plaines, Ill. Examples of commercial alpha amylase preparation which can be used herein include Amalase THC from G.B. Fermentation Inc., and Termamyl 60L and Termamyl 60G from Novo Industri A/S. An example of a commercial enzyme preparation containing a mixture of alpha amylases and alkaline proteases which can be used herein is Maxatase P from G.B. Fermentation Inc.

The commercial enzyme preparation preferred for use herein is Savinase 8.0 Slurry from Novo Industries, an alkaline proteolytic enzyme preparation obtained from the genus Bacillus Subtilis containing about 6% by weight of the enzyme and having an activity of 8 kilo novo units.

As is well known in the art the carriers, particularly calcium salt carriers, help stabilize the enzymes by putting stabilizing ions into solution. However, although such commercial enzyme preparations employing the aforementioned carriers exhibit more stability than the pure enzyme, even greater stability is generally desired.

Compositions of this invention will stabilize from about 0.006% to about 5.0% of an active enzyme, the preferred amount of enzyme being from about 0.006% to about 2.5% by weight.

The stabilizing agents which stabilize the enzymes described above are the esters of the formula RCOOR', wherein R is an alkyl radical of from one to three carbon atoms or hydrogen and R' is an alkyl radical of from one to six carbon atoms. Hence, the ester stabilizers include ethyl formate, ethyl acetate, amyl acetate, methyl acetate, ethyl propionate, butyl acetate, and methyl butyrate. These esters can be used in effective amounts, ranging from about 0.1% to about 2.5% by weight of the composition. The preferred ranges for these agents are from about 0.25% to about 1.5% by weight of the composition, while the most preferred range is from about 0.5 to about 1.0. It is noted that the ester stablizers have low solubilities, and that the concentration of ester in the compositions of the present invention should be below the solubility limit of the ester used. In general, a problem may occur only with the higher molecular weight esters, which have the lowest solubility.

In addition to the essential ingredients described above the composition of this invention can contain other ingredients such as surfactants of either the nonionic or anionic type, organic solvents, solubilizing compounds and perfumes.

Inclusion of a surfactant of either the nonionic or anionic type is advantageous in that they tend to enhance the enzymatic stability of these compositions, however, more importantly they significantly provide detergent characteristics to these compositions. The nonionics or anionics may be utilized in amounts up to about 55% and preferably from about 5% to about 30% by weight of the total composition.

Examples of suitable nonionics include:

(1) Ethoxylated fatty alcohols—having the formula: $RO—(CH_2CH_2O)_nH$ where R is from 8 to 18 carbon atoms and n is an integer of from 1 to 500.

Examples of these are:

(a) the condensation product of 1 mole of an aliphatic alcohol, having from 12 to 13 carbon atoms in either a straight or branched chain configuration, with an average of 6.5 moles of ethylene oxide;
(b) the condensation product of 1 mole of an aliphatic alcohol, having from 12 to 15 carbon atoms in either a straight or branched chain configuration, with 9 moles of ethylene oxide, and
(c) the condensation product of 1 mole of an aliphatic alcohol, having between 12 and 15 carbon atoms in either the straight or branched chain configuration, with 3 moles of ethylene oxide.

Examples of (a), (b) and (c) are commercially available from the Shell Oil Company under the trade names of Neodol, Neodol 23-6.5, Neodol 25-9, and Neodol 25-3, respectively.

(2) Ethoxylated fatty acids—having the formula:

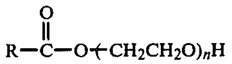

where R and n are as in (1).

(3) Ethoxylated alkyl phenols—having the formula:

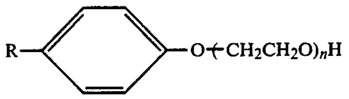

wherein R is an alkyl radical having from 6 to 16 carbons and n is an integer from 1 to 500.

Examples of suitable anionics include:

(1) Soaps—having the formula:

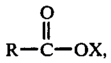

where X is sodium, potassium or ammonium and R is a saturated or unsaturated branched, or straight chain fatty acid radical having from 10 to 18 carbon atoms.

(2) Alkyl benzene sulfonates—having the formula:

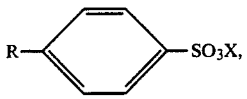

where X is ammonium, triethanolammonium, sodium or potassium and R is an alkyl radical having from 8 to 18 carbon atoms.

(3) Hydroxy alkane sulfonates—having the formula:

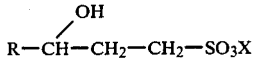

where X is as in (2) and R is an alkyl radical having from 10 to 15 carbon atoms.

(4) Sulfonated fatty acids—having the formula:

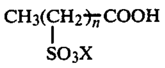

where X is as in (2) and n is an integer between 12 and 18.

(5) Sulfonated nonionics—having the formula:

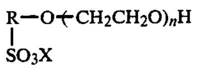

where X is as in (2) and n is an integer from 8 to 16 where R is as in (1).

(6) Fatty alcohol sulfates—having the formula: $CH_3(CH_2)_nCH_2O—SO_3X$ where X is as in (2) and n is an integer from 8 to 16.

(7) Sulfated nonionics—having the formula: $RO—CH_2CH_2O)_nSO_3X$ where X is as in (2), R is an alkyl radical having from 12 to 18 carbon atoms and n is an integer from 1 to 50.

(8) Mono- and di-esters of sodium sulfosuccinates—having the formula:

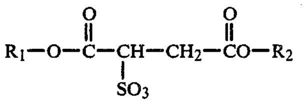

where $R_1$ is either sodium, hydrogen or an alkyl radical having from 1 to 12 carbon atoms and $R_2$ is an alkyl radical having from 1 to 12 carbon atoms.

The surfactants which are preferred are the nonionics of the ethoxylated fatty alcohol type.

The compositions of this invention can also contain organic solvents such as the isoparaffinic mixtures of petroleum distillates. These may be added in amounts of up to 75% by weight with about 10% to about 40% by weight being the amount preferred.

Compositions containing the organic solvents set forth above can also contain solubilizing compounds. Examples of such compounds are the sodium salts of benzene sulfonate, toluene sulfonate, and xylene sulfonate. These agents can be added in amounts of up to about 10% by weight, however about 3% to about 6% by weight of these agents is the preferred amount for inclusion.

In addition to the various ingredients recited above the compositions of this invention can also contain optical brighteners, fabric softeners, anti-static agents, anti-redeposition agents and small amounts of perfume and dye.

The pH of these compositions will generally be around 7. Depending on the enzyme being used, the pH can be raised by adding sodium hydroxide or lowered by adding acetic acid. It is particularly preferred to incorporate a buffering agent, for example, sodium acetate or other alkali metal ammonium of alkanol ammonium acid salt of one to four carbon atoms, which agent does provide some stabilizing effect. As shown in the examples below whatever benefit is obtained by the buffering agent is enhanced by the ester stabilizers of the present invention. The salt may be incorporated in an amount of from 0.1 to 10% by weight.

The various components of the enzyme containing compositions can be mixed together in any order. However, it is preferred that an ester and water mixture be prepared first, and that the enzymes be added thereto to prevent any degradation or deactivation of the enzyme. The optional components such as the surfactants can be added at any time.

There are a variety of uses for the compositions of this invention. For example they may be used as spot removers. They may also be used in home laundering operations as presoaks and as laundry additives for use during the wash cycle of an automatic washer.

The following Example illustrates the invention:

The following compositions were prepared and stored in closed-glass containers at 100° F. for the indicated periods of time. It is estimated that one week's storage at 100° F. is equal to between about 2 to 3 months at storage at room temperature.

The pH of each of the following compositions was about 7.

| | Sample No. | | | | | | | | | | |
|---|---|---|---|---|---|---|---|---|---|---|---|
| | 1 | 2 | 3 | 4 | 5 | 6 | 7 | 8[5] | 9[5] | 10[5] | 11[5] |
| | | | | | Composition (Wt. %) | | | | | | |
| Ingredients | | | | | | | | | | | |
| Neodol 25-9[1] | 5 | 5 | 5 | 5 | 5 | 5 | 5 | 5 | 2.5 | 2.5 | 5 |
| Neodol 23-6.5[2] | 5 | 5 | 5 | 5 | 5 | 5 | 5 | 5 | 2.5 | 2.5 | 5 |
| Savinase 8.0[3] Slurry | 1 | 1 | 1 | 1 | 1 | 1 | 1 | 1 | 1 | 1 | 1 |
| Sodium Acetate | 1 | 1 | 2 | 2 | 2 | 2 | 2 | 2 | 0 | 4 | 1 |
| Ethyl Acetate | 1 | 0 | 0.5 | 2 | 0 | 0 | 0.5 | 0 | 0 | 0 | 0 |
| Amyl Acetate | 0 | 1 | 0 | 0 | 0.5 | 2 | 0 | 0 | 0 | 0 | 0 |
| Water | 87 | 87 | 86.5 | 85 | 86.5 | 85 | 86.5 | 87 | 94 | 90 | 88 |
| | | | | | Activity (%)[4] | | | | | | |
| Initial Activity | 100 | 100 | 100 | 100 | 100 | 100 | 100 | 100 | 100 | 100 | 100 |
| Act. After 2 Weeks | | | 79 | 81 | 83 | 83 | 80 | 64 | 56 | | |
| Act. After 4 Weeks | 65 | 62 | 75 | | | | 74 | | | | 53 |
| Act. After 6 Weeks | | | 63 | 60 | 51 | 61 | 63 | 44 | 21 | 45 | |
| Act. After 8 Weeks | 35 | 49 | 57 | 44 | 46 | 55 | | 39 | 18 | 37 | 34 |

[1]Nonionic surfactant comprised of an ethoxylated alcohol where one mole of aliphatic alcohol having from 12 to 15 carbon atoms was ethoxylated with an average of 9 moles of ethylene oxide.
[2]Nonionic surfactant comprised of an ethoxylated alcohol where one mole of aliphatic alcohol having from 12 to 13 carbon atoms was ethoxylated with an average of 6.5 moles of ethylene oxide.
[3]A commercial alkaline proteolytic enzyme preparation available from Novo Industries containing 6% active enzymes with an activity of 8.0 Kilo Novo protease units.
[4]Percent remaining activity was determined by trinitrobenzene sulfonate method using casein as a substrate. Activity values are subject to an experimental error of ±10% in runs 1-2 and ±5% in runs 3-11.
[5]Sample numbers 8-11 are not in accordance with the present invention and have been included for the purpose of comparison only.

As shown in the Table significant improvement is obtained with small amounts of the ester stabilizer of the present invention. Thus, for example, after two weeks the percent active enzyme in Sample No. 3 is about 23% greater than in Sample No. 9. After four weeks the percent active enzyme in Sample No. 3 is about 42% greater than Sample No. 11, and after eight weeks about 68% greater.

Having described some typical embodiment of this invention it is not my intent to be limited to the specific details set forth herein, Rather, I wish to reserve to myself any variations or modifications that may appear to those skilled in the art and fall within the scope of the following claims.

I claim:

1. An aqueous-based enzyme containing composition wherein the enzymes have enhanced stability against loss of activity, the composition consisting essentially of on a weight basis:

(a) from 0 to about 55% of a surfactant selected from the group consisting of anionic and nonionic surfactants, and mixtures thereof:

(b) from about 0.006 to about 5% of an active enzyme selected from the group consisting of protease and alpha amylase enzymes, and mixtures thereof, said enzyme being provided in pure form or as incorporated within a commercial enzyme preparation comprising from 2 to about 80% of said enzyme and from about 20 to about 98% of a carrier therefor;

(c) from about 0.1% to about 2.5% of an ester of the formula RCOOR' wherein R is an alkyl radical of from one to three carbons or hydrogen and R' is an alkyl radical of from one to six carbon atoms; and (d) the remainder water.

2. The composition of claim 1 wherein the carrier is selected from the group consisting of sodium chloride, sodium sulfate, calcium sulfate, glycerol, and combinations of same.

3. The composition of claim 1 further including from about 0.1 to about 10% of an alkali metal, ammonium or alkanol ammonium salt of a carboxylic acid of from one to four carbon atoms.

4. The composition of claim 3 wherein the ester is selected from the group consisting of ethyl acetate, methyl acetate, ethyl propionates, butyl acetate, methyl butyrate, ethyl formate, amyl acetate and amyl formate.

5. The composition of claim 4 wherein the salt is sodium acetate.

6. The composition of claim 4 wherein the percent by weight of the ester is from about 0.25 to about 1.5%.

7. The composition of claim 1 wherein the percent by weight of the surfactant is from about 5% to about 30%.

8. The composition of claim 6 wherein the percent by weight of water is from about 40% to about 95%.

9. The composition of claim 6 wherein the percent by weight of the enzyme is from about 0.006% to about 2.5%.

10. The composition of claim 9 wherein the pH is from about 6 to about 9.

11. The composition of claim 10 wherein the enzyme is a proteolytic enzyme obtained from the Bacillus Subtilis.

12. The composition of claim 11 wherein the ester is selected from the group consisting of ethyl acetate and amyl acetate.

13. The composition of claim 12 wherein the percent by weight of the ester is from about 0.25 to about 1.5%, and wherein the salt is sodium acetate in an amount of between about 0.5 to about 4%.

14. The composition of claim 12 wherein the carrier is selected from the group consisting of sodium chloride, sodium sulfate, calcium sulfate, glycerol, and combination of same.

15. The composition of claim 12 wherein the percent by weight of the surfactant is about 30% and wherein the surfactant is a mixture comprised of about 33.3% by weight of an anionic surfactant and about 66.6% by weight of a nonionic surfactant.

16. The composition of claim 15 wherein the nonionic surfactant is an ethoxylated fatty alcohol having the formula $RO-(CH_2CH_2O)_n-H$ where R is from 8 to 18 carbon atoms and n is an integer from 1 to 500.

17. The composition of claim 16 wherein the nonionic surfactant is a mixture of:

(a) the condensation product of 1 mole of an aliphatic alcohol having from 12 to 13 carbon atoms in either a straight or branched chain configuration, with an average of 6.5 moles of ethylene oxide, and (b) the condensation product of 1 mole of an aliphatic alcohol, having from 12 to 15 carbon atoms in either a straight or branched chain configuration, with 9 moles of ethylene oxide.

18. The composition of claim 17 wherein the nonionic surfactant mixture is comprised of about 50% by weight of component (a) and about 50% by weight of component (b).

19. The composition of claim 18 further including by weight of the composition:

(a) from about 1% to about 10% of a solubilizing compound, and (b) from 1% to about 75% of an isoparaffinic mixture of petroleum distillates having an average molecular weight of about 154.

20. The composition of claim 19 wherein the solubilizing agent is between about 3% to about 6% by weight of the composition; wherein the isoparaffinic mixture of petroleum distillates is from about 10% to about 40% by weight of the composition, and wherein the solubilizing agent is sodium xylene sulfonate.

* * * * *